United States Patent [19]

deLearie et al.

[11] Patent Number: 5,508,388
[45] Date of Patent: Apr. 16, 1996

[54] PROCESS FOR MANUFACTURING DTPA-BIS AMIDE MAGNETIC RESONANCE IMAGING

[75] Inventors: Lynn deLearie, University City; Wayne H. Lin, Huntleigh; Dennis A. Moore, Ferguson; David H. White, Ballwin, all of Mo.

[73] Assignee: Mallinckrodt Medical, Inc., St. Louis, Mo.

[21] Appl. No.: 437,915

[22] Filed: May 10, 1995

Related U.S. Application Data

[63] Continuation of Ser. No. 916,227, Jul. 16, 1992, abandoned.

[51] Int. Cl.$^6$ ............................................. C07F 5/00
[52] U.S. Cl. .................................................. 534/16
[58] Field of Search ..................... 534/15, 16; 556/40, 556/50, 63, 148; 424/9.364

[56] References Cited

U.S. PATENT DOCUMENTS

| | | | |
|---|---|---|---|
| 4,687,658 | 8/1987 | Quay | 424/9 |
| 4,687,659 | 8/1987 | Quay | 424/9 |
| 4,826,673 | 5/1989 | Dean et al. | 424/9 |
| 5,130,120 | 7/1992 | Weber | 424/9 |
| 5,137,711 | 8/1992 | Weber et al. | 424/9 |

OTHER PUBLICATIONS

Merck Index, *10th Edition*, 1983, p. 10, 749.

Riddick et al., *Organic Solvent*, 1970, pp. 798–799.

*Primary Examiner*—Shean C. Wu
*Assistant Examiner*—Lara E. Chapman
*Attorney, Agent, or Firm*—Brian K. Stierwalt

[57] ABSTRACT

Processes for manufacturing diethylenetriaminepentaacetic acid ("DTPA") bis(amide) magnetic resonance imaging ("MRI") agents are disclosed. Specifically, processes for manufacturing [N,N"-Bis[N-(2-methoxyethyl)carbamoylmethyl]diethylenetriamine-N,N',N"-triacetato]gadolinium(III) are disclosed.

23 Claims, No Drawings

PROCESS FOR MANUFACTURING DTPA-BIS AMIDE MAGNETIC RESONANCE IMAGING

This is a continuation of Ser. No. 07/916,227 filed Jul. 16, 1992 now abandoned.

BACKGROUND OF THE INVENTION

This invention relates to processes for manufacturing diethylenetriamine-pentaacetic acid ("DTPA") bis(amide) magnetic resonance imaging ("MRI") agents. More specifically, the present invention includes processes for manufacturing [N,N"-Bis[N-(2-methoxyethyl)carbamoylmethyl]diethylenetriamine-N,N', N"-triacetato]-gadolinium(III).

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution and/or the relaxation times in organs and tissues. The technique of MRI is advantageously non-invasive as it avoids the use of ionizing radiation.

It is known to administer divalent and trivalent paramagnetic ions in the form of complexes with organic complexing agents as magnetic resonance contrast agents. Such complexes provide the paramagnetic ions in a soluble, non-toxic form, and facilitate their rapid clearance from the body following the imaging procedure. Gries et. al., U.S. Pat. No. 4,647,447, disclose complexes of various paramagnetic ions with conventional aminocarboxylic acid complexing agents. A preferred complex disclosed by Gries et. al. is the complex of gadolinium(III) with diethylenetriamine-pentaacetic acid ("DTPA") represented by the formula:

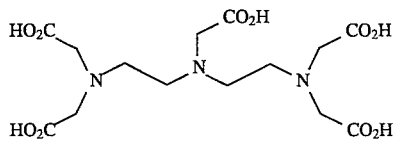

Paramagnetic ions, such as gadolinium(III), have been found to form strong complexes with ethylenediaminetetraacetic acid ("EDTA") represented by the formula:

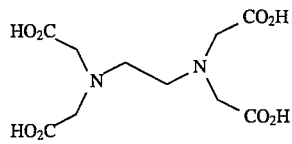

and with tetraazacyclododecane-N,N', N", N"-tetraacetic acid ("DOTA") represented by the formula:

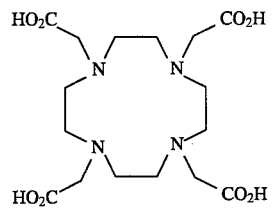

These complexes do not dissociate substantially in physiological aqueous fluids. The gadolinium complex of DTPA has a net charge of −2, whereas the gadolinium complex of EDTA and DOTA has a net charge of −1, and both are generally administered as soluble salts. Typical such salts are sodium and N-methylglucamine. The administration of such salts is attended by certain disadvantages. These salts can raise the in vivo ion concentration and cause localized disturbances in osmolality, which in turn, can lead to edema and other undesirable reactions.

Efforts have been made to design new ionic and neutral paramagnetic metal complexes which avoid or minimize the above mentioned disadvantages. In general, this goal can be achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et. al., U.S. Pat. No. 4,826,673 discloses mono—and polyhydroxyalkylamide derivatives of DTPA and their use as complexing agents for paramagnetic ions. It can also be achieved by covalent attachment of organic cations to the complexing agent in such a manner that the sum of positive and negative charges in the resulting metal complex is zero.

R. W. Webber, in U.S. Pat. No. 5,130,120 and Webber et. al. in U.S. patent application Ser. No. 07/377,491, now U.S. Pat. No. 5,137,711, which are incorporated herein by reference, disclose paramagnetic DTPA and EDTA alkoxyalkylamide complexes as magnetic resonance imaging agents. These patents disclose suitable processes for preparing amide derivatives of DTPA and EDTA in the laboratory. However, the disclosed processes include reaction conditions and solvents which are not suitable for manufacturing large quantities of the magnetic resonance imaging agent.

Thus, there is a need in the art for processes for manufacturing diethylenetriamine-pentaacetic acid (DTPA)-bis(amide) magnetic resonance imaging agents.

Such manufacturing processes are disclosed and claimed herein.

SUMMARY OF THE INVENTION

The present invention provides manufacturing processes for DTPA-bis(amide) magnetic resonance imaging agents. The overall manufacturing process can be divided into three general steps: (1) preparation of DTPA-bis(anhydride), (2) reaction of the DTPA-bis(anhydride) with a suitable amine to form a DTPA-bis(amide) complexing agent, and (3) formation of a paramagnetic metal complex with the DTPA-bis(amide) complexing agent. The final product, the paramagnetic metal complex, may be prepared either after isolation of the DTPA-bis(amide) complexing agent or in situ.

DTPA-bis(anhydride) is prepared by reacting DTPA and acetic anhydride. Acetic acid is produced as a byproduct and must be neutralized with a base. Of the possible bases which may be used, pyridine is currently preferred because it results in a high purity final product. In step 1, preparation of DTPA-bis(anhydride), DTPA, acetic anhydride, pyridine, and acetonitrile are combined in a suitable reactor equipped with a mechanical stirrer and a reflux condenser attached to a $CaSO_4$ dry tube. The mixture is heated with stirring at a temperature in the range from 55° C.–65° C. overnight (about 18 hours). The general reaction of step 1, is shown below:

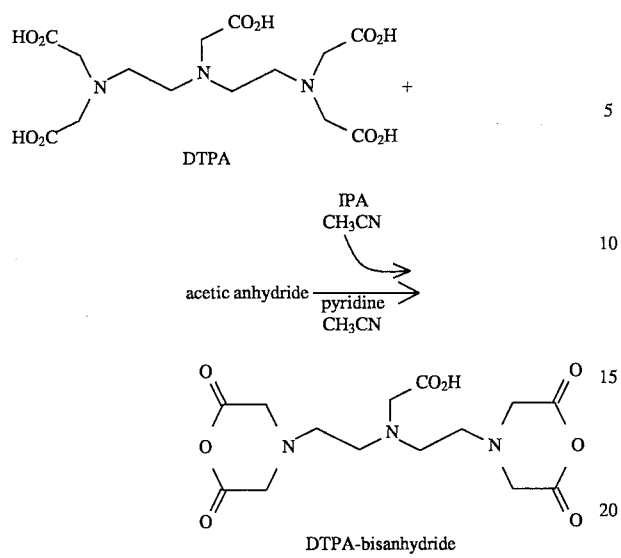

Although pyridine is used to neutralize the acetic acid produced during the anhydride reaction, pyridine is highly toxic and relatively expensive. Therefore, the amount of pyridine used in the process is reduced to the minimum required to form the desired bis(anhydride).

In step 2 process of the present invention, the DTPA-bis(anhydride) is reacted with a suitable primary or secondary amine to form a DTPA-bis(amide) complexing agent. Suitable primary or secondary amines include lower (such as $C_{1-6}$) alkylamine; monohydroxyalkylamine; polyhydroxyalkylamine; alkoxyalkylamine; polyalkoxyalkylamine; di(alkyl)amine; di(monohydroxyalkyl)amine; di(polyhydroxyalkyl)amine; di(alkoxyalkyl)amine; di(polyalkoxyalkyl)amine; alkyl, monohydroxyalkylamine; alkyl, polyhydroxyalkylamine; alkyl, alkoxyalkylamine; alkyl, polyalkoxyalkylamine; monohydroxyalkyl, polyhydroxyalkylamine; monohydroxyalkyl, alkoxyalkylamine; monohydroxyalkyl, polyalkoxyalkylamine; polyhydroxyalkyl, alkoxyalkylamine; polyhydroxyalkyl, polyalkoxyalkylamine; and alkoxyalkyl, polyalkoxyalkylamine.

DTPA-bis(anhydride), in the form of a dry or wet solid, is suspended in a suitable inert solvent, such as 2-propanol, acetonitrile, dioxane, tetrahydrofuran, t-butanol, sec-butanol, and mixtures thereof, and reacted with the primary or secondary amine. The mixture is heated with stirring for sufficient time to complete the reaction. Selected cosolvents are added and the reaction mixture is heated or refluxed to dissolve DTPA-bis(amide) product, but not undesirable impurities. Typical cosolvents include 2-propanol, ethanol, water, methanol, and mixtures thereof. After cooling, the mixture was filtered to remove solid impurities, such as DTPA. At this stage, the DTPA-bis(amide) may be isolated by crystallization or reacted with a desired paramagnetic metal ion to form a metal complex.

The general reaction of step 2, in which the reactive amine is 2-methoxyethylamine (MEA), is shown below:

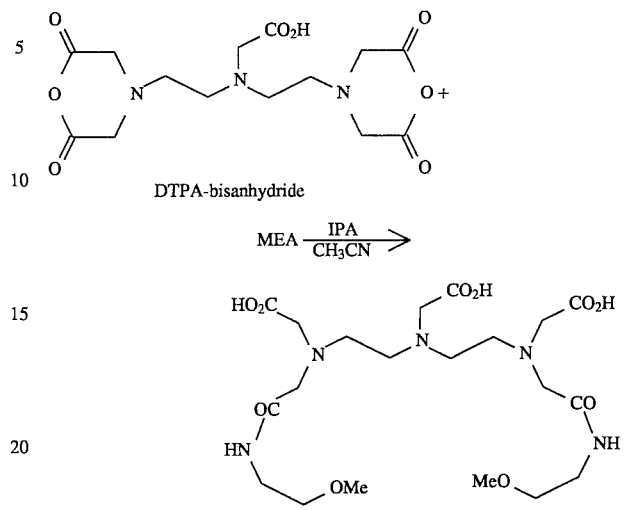

Formation of a paramagnetic metal complex with the DTPA-bis(amide) complexing agent, step 3, generally involves refluxing the complexing agent with the paramagnetic metal ion until the desired complex is formed. Typical reflux temperatures are in the range from 70° C. to 100° C. and reflux time from 2 to 24 hours. Typical paramagnetic metals which may be used include: chromium(III), manganese(II), manganese(III), iron(III), iron(II), cobalt(II), nickel(II), copper(II), praseodymium(III), europium(III), neodymium(III), samarium(III), ytterbium(III), gadolinium(III), terbium(III), dysprosium(III), holmium(III), and erbium(III). Gadolinium(III) ions have been particularly preferred as MRI contrasting agents. The paramagnetic metals are typically in the form of inorganic oxides, carbonates, and hydroxides.

The general complexation reaction can be illustrated by the reaction of N,N''-Bis[N-(2-methoxyethyl)carbamoylmethyl]diethylenetriamine-N,N',N''-triacetic acid with $Gd_2O_3$ as shown below:

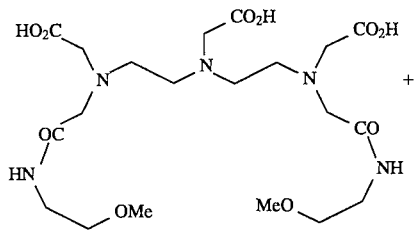

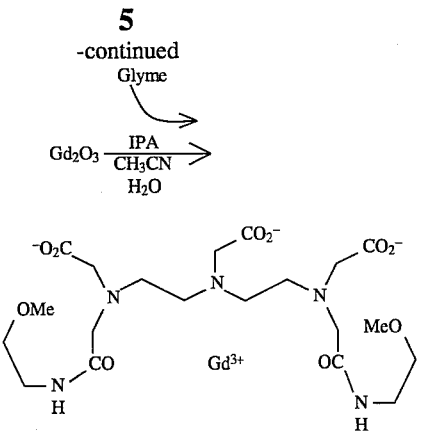

The reaction mixture is filtered to remove insoluble impurities. If the final paramagnetic metal complex is insoluble in the reaction mixture, then a cosolvent may be added to dissolve the complex and enable removal of insoluble impurities by filtration. A crystallization solvent, such as ethanol, acetonitrile, methanol, glyme, 2-propanol, methylethyl ketone, acetone, and mixtures thereof may be added to affect crystallization of the final paramagnetic metal complex.

DETAILED DESCRIPTION OF THE PREFERRED EMBODIMENTS

The present invention provides processes for manufacturing DTPA-bis(amide) paramagnetic metal complexes useful as magnetic resonance imaging agents. Although most of the following discussion will focus on one particularly useful DTPA-bis(amide) paramagnetic metal complex, [N,N"-Bis [N-(2-methoxyethyl)carbamoylmethyl]diethylenetriamine-N,N',N"-triacetato]-gadolinium(III), those skilled in the art can adapt the disclosed manufacturing processes for use in preparing other DTPA-bis(amide) paramagnetic metal complexes useful as magnetic resonance imaging agents.

The overall manufacturing process can be divided into three general steps: (1) preparation of DTPA-bis(anhydride), (2) reaction of the DTPA-bis(anhydride) with a suitable amine to form a DTPA-bis(amide) complexing agent, and (3) formation of a paramagnetic metal complex with the DTPA-bis(amide) complexing agent. These steps are described above in general terms.

The following examples are offered to further illustrate specific aspects of the present invention. These examples are intended to be purely exemplary and should not be viewed as a limitation on any claimed embodiment.

Example 1

Preparation of DTPA-Bis(Anhydride)

DTPA (227 g, 0.577 mole), acetic anhydride (164 ml, 1.74 mole), pyridine (221 ml, 2.60 mole), and acetonitrile (114 ml) are combined in a 1 L, 3-necked round-bottomed flask equipped with a thermometer, a mechanical stirrer, and a reflux condenser attached to a $CaSO_4$ dry tube. The mixture is heated with stirring in a 55° C.–65° C. oil bath overnight (about 18 hours). The reaction mixture is cooled to room temperature in a water bath. The product is collected by filtration in vacuo using a filter cloth. 2-propanol (100 ml) is used to rinse the reactor and carefully added to the DTPA-bis(anhydride) cake as soon as the liquid disappeared from the bis(anhydride) surface. It is important that subsequent washings proceed in the same fashion.

The product is further washed with 2-propanol (350 ml) and then acetonitrile (340 ml). The filtration funnel containing the product is covered with a tight cover connected to a DRIERITE dry tower. The other end of the dry tower is opened to the atmosphere. DTPA-bis(anhydride) is dried at room temperature under vacuum for about 20 minutes. The acetonitrile wet DTPA-bis(anhydride) cake is dried at room temperature in vacuo (0.05 mmHg) to a constant weight. The percent yield of the dried bis(anhydride) is 95–99%.

Example 2

Effect of Temperature and Acetonitrile on the Preparation of DTPA-bis(anhydride)

A series of experiments for the preparation of DTPA-bis(anhydride) at various temperatures between 55° C. to 74° C. were studied. The experiments were carried out with the molar ratio of DTPA, acetic anhydride, and pyridine held constant at 1.0:3.0:4.5, respectively. This molar ratio was determined previously to be an optimum for the reaction. The reactions were preformed for 18–22 hours using an oil-bath for more precise temperature control. A second set of experiments was performed in which acetonitrile was used as a diluent in the preparation.

To determine the result of a reaction, the completion of the reaction and the quality of the produced anhydride were evaluated. The completion of the reaction was determined by subtracting the amount of DTPA recovered from the subsequent reaction of DTPA-bis(anhydride) with 2-methoxyethylamine (MEA) from the amount of DTPA used in the preparation. The quality of the anhydride was determined after isolation by the color of DMSO solution and by $^1$HNMR.

Based upon the results, it was concluded that DTPA-bis(anhydride) was best prepared between 55° C. and 65° C. with 0.5 ml acetonitrile per gram of DTPA used in the reaction. When acetonitrile was used, the reaction mixture was relatively fluid which enabled the reaction slurry to be drained from the reactor.

Example 3

Effect of Reaction Time on the Percent Completion of the DTPAA-bis (anhydride) Synthesis The reaction time required for the preparation of DTPA-bis(anhydride) was studied. The effect of the reaction time on the percent completion of DTPA-bis(anhydride) was determined at 64° C. to 66° C. using an oil bath. The percent completion of a reaction was calculated as described above in Example 1. The results are given in Table I.

TABLE I

| The Effect of the Reaction Time on the Percent Completion of the DTPA-bis(anhydride) Synthesis | |
|---|---|
| Reaction Time (hours) | % Completion |
| 3.0 | 75.8 |
| 5.0 | 86.4 |
| 18 | >99.0 |
| 22 | >99.0 |

Based on the above results, it was concluded that DTPA-bis(anhydride) was best prepared overnight.

Example 4

Stability of Acetonitrile Wet DTPA-bis(ahydride)

In this study, DTPA was prepared using the above mentioned procedure. The DTPA-bis(anhydride) was isolated and washed with isopropyl alcohol first and then with acetonitrile. The product was stored as an acetonitrile wet cake in a tightly sealed container at room temperature. The actual contents of DTPA-bis(anhydride) were determined by LOD of the wet sample in vacuo at room temperature. The drying procedure of 50 g of wet DTPA-bis(anhydride) took about 2 hours. The proton NMR spectra of the acetonitrile wet DTPA-bis(anhydride) was taken from Day 0 to Day 15 and showed that the anhydride decomposed very slowly. A reasonably good NMR spectrum was obtained after the material had been stored for 8 days.. A 91.3% yield of crystalline [N,N"-Bis[N-(2-methoxyethyl)carbamoylmethyl]-diethylenetriamine-N,N',N"-triacetato]-gadolinium(III) was obtained from 14 day old acetonitrile wet DTPA-bis(anhydride).

Example 5

Preparation of N,N"-Bis[N-(2-methoxyethyl)carbamoylmethyl]-diethylenetriamine-N,N', N"-triacetic acid DTPA-bis(anhydride) (dried, 125.3 g, 0.351 mole), 2-propanol (250 ml, 2.0 mLs/g DTPA-bis(anhydride)), acetonitrile (125 ml, 1.0 mLs/g DTPA-bis(anhydride)), and 2-methoxyethylamine (52.7 g, 0.702 mole, 2.00 equivalents of DTPA-bis(anhydride)) were heated with stirring at 55° C. to 65° C. overnight. 2-propanol (63 ml, such that the total 2-propanol used was 313 ml (2.5 times DTPA-bis(anhydride)) and ethanol (reagent, absolute, 250 ml) were added to the mixture. The mixture was heated to boil (76°–77° C.) and refluxed for 10 to 20 minutes to dissolve the solid. After cooling to room temperature, the mixture was filtered to remove DTPA. Ethanol (reagent, absolute, 63 ml) was used to rinse the reactor and the funnel. The total ethanol used was 313 ml (2.5 time DTPA-bis(anhydride)). A small amount of crystalline N,N"-Bis[N-(2-methoxyethyl)carbamoylmethyl]diethylenetriamine-N,N',N"-triacetic acid was added to the titrate to initiate the crystallization. The mixture was allowed to stir (low speed) overnight at room temperature. The N,N"-Bis[N-(2-methoxyethyl)carbamoylmethyl]diethylenetriamine-N,N',N"-triacetic acid crystals were collected by filtration and were washed with 75 ml ethanol. The N,N"-Bis[N-(2-methoxyethyl)carbamoylmethyl]diethylenetriamine-N,N',N"-triacetic acid crystals were dried to a constant weight in vacuo.

Example 6

Preparation of N,N"-Bis[N-(2-methoxyethyl)carbamoylmethyl]-diethylenetriamine-N,N',N"-triacetic acid Acetonitrile wet DTPA-bis(anhydride) containing 89.0% DTPA-bis(anhydride) (217.0 g, equivalent to 193.1 g DTPA-bis(anhydride), 0.540 mole), 2-propanol (290 ml), acetonitrile (193 ml) were mixed in a 2 L round-bottomed flask equipped with a thermometer, an overhead stirrer, and a reflux condenser. 2-methoxyethylamine (81.1 g, 1.08 mole) was added to the mixture at a rate to keep the reaction temperature at or below 65° C. The addition of MEA took about 5 minutes. The reactor was heated with stirring in a 60° C. to 70° C. oil bath for 3 hours. At the end of the reaction, the reaction mixture was 62° C. and had become homogeneous. The reaction mixture was cooled to room temperature and a cosolvent, methanol (290 ml) was added to the mixture. The solution was filtered through a filter cloth to remove DTPA (trace). Methanol (290 ml) was used to rinse the reactor and filtering equipment.

Glyme (1160 ml) was slowly added to the combined solution of liltrate and rinsed. The solution became slightly milky and was seeded with solid N,N"-Bis[N-(2-methoxyethyl)carbamoylmethyl]diethylenetriamine-N,N',N"-triacetic acid. The solution was allowed to stir overnight at room temperature while the solids precipitated. Solid N,N"-Bis[N-(2-methoxyethyl)carbamoylmethyl]diethylene-triamine-N,N',N"-triacetic acid was collected by filtration using a filter cloth. The product was washed on the funnel using 800 ml of a washing solvent containing methanol and glyme in the ratio of 1 to 3 (V/V), respectively. The product was dried in a vacuum oven at 45° C.–50° C. to a constant weight. The dried product was 230.2 g (83.9% yield).

Example 7

Reaction Time for Synthesis of N,N"-Bis[N-(2-methoxyethyl)carbamoylmethyl]-diethylenetriamine-N,N",N"-triacetic acid The time for the reaction of DTPA-bis(anhydride) with 2-methoxyethylamine (MEA) was studied at 52° C. and 67° C. using a mixture of 2-propanol and acetonitrile as solvent. At these two temperatures, the reactions were completed in 2.0 hours and 45 minutes, respectively. The completion of the reaction was determined by the homogeneity of the reaction mixture and the disappearance of MEA by TLC. After work up, both reactions produced high quality N,N"-Bis[N-(2-methoxyethyl)carbamoylmethyl]diethylenetriamine-N,N',N"-triacetic acid in 81.3% and 80.8% yields, respectively. It was concluded that, for convenience, the reaction of DTPA-bis(anhydride) with MEA in 2-propanol and acetonitrile should be done in 3.0 hours at a temperature between 55° C.–65° C.

Example 8

Effec to form the MEA to DTPA-bis(anhydride) Ratio on the N,N"-Bis[N-(2-methoxyethyl)carbamoylmethyl]-diethylenetriamine-N,N',N"-triacetic Acid Quality and Percent Yield The effect of the 2-methoxyethylamine (MEA) to DTPA-bis(anhydride) ratio on the quality and percent yield of N,N"-Bis [N-(2-methoxyethyl)carbamoylmethyl]diethylene-triamine-N,N', N"-triacetic acid was studied. The reactions were carried out at 58° C. to 60° C. for 3.0 hours using 2-propanol and acetonitrile as solvent. The percent yield of N,N"-Bis[N-(2-methoxyethyl)carbamoylmethyl]diethylene-triamine-N,N',N"-triacetic acid and the amounts of major impurities in the products are shown in Table II.

TABLE II

The Effect of MEA to DTPA-bis(anhydride) Ratio on the Percent Yield and Quality of DTPA-bio(amide) Complexing Agent

| MEA/ DTPAba | % Yield* | % Chrom Purity | DTPA (w/w %) | MEA (w/w %) | Monoamide (w/w %)† |
| --- | --- | --- | --- | --- | --- |
| 1.8 | 92.5 | 98.7 | <0.06 | <0.010 | 0.5–1.0 |
| 1.9 | 90.3 | 98.7 | <0.06 | <0.010 | 0.5–1.0 |
| 2.0 | 94.8 | 99.0 | <0.06 | <0.010 | <0.1 |
| 2.1 | 85.5 | 99.4 | <0.06 | <0.010 | <0.1 |

$$*\% \text{ Yield} = \frac{(Wt.\ of\ product) \times (\%\ of\ DTPA\text{-}bis(amide)\ in\ the\ product)}{Theoretical\ yield\ based\ on\ DTPA\text{-}bis(anhydride)}$$

†Because of the lack of monoamide standard, the numbers in this column were estimated from the capillary zone electrophoresis curve.

A significantly lower percent yield from the MEA/DTPA-bis(anhydride)=2.1 reaction was attributed to the formation of a MEA-DTPA-bis(amide) salt. This salt was removed as an impurity in the purification process. Nevertheless, both MEA/DTPA-bis(anhydride) equal to 2.0 and 2.1 reactions produced N,N"-Bis[N-(2-methoxyethyl)carbamoylmethyl] diethylenetriamine-N,N',N"-triacetic acid containing low monoamide.

Based on the high percent yield and high purity of the product, it was concluded that the N,N"-Bis[N-(2-methoxyethyl)carbamoylmethyl] diethylenetriamine-N,N',N"-triacetic acid was best synthesized using the mole ratio of MEA to DTPA-bis(anhydride) equal to 2.0.

Example 9

Preparation of [N,N"-Bis[N-(2-methoxyethyl)carbamoylmethyl]diethylenetriamine-N,N',N"-triacetato]-gadolinium (III)

N,N',-Bis[N-(2-methoxyethyl)carbamoylmethyl] diethylenetriamine-N,N',N"-triacetic acid (herein referred to as "complexing agent", dried, 120.0 g, 0.236 mole), water (84 ml, 0.7 mLs/g complexing agent), 2-propanol (132 ml, 1.1 mLs/g complexing agent), acetonitrile (84 ml, 0.7 mLs/g complexing agent), and $Gd_2O_3$ (40.8 g, 0.113 moles=0.479 equivalents of the complexing agent) were heated with stirring at reflux (77° C.) overnight. After cooling to room temperature, the mixture was filtered to remove insoluble solids. Acetonitrile (300 ml, 2.5 mLs/g complexing agent) was added slowly to the filtrate with stirring. (The total amount of acetonitrile used was 384 ml (3.2 mLs/g complexing agent)). A small amount of crystalline [N,N"-Bis[N-(2-methoxyethyl)carbamoylmethyl]diethylenetriamine-N,N',N"-triacetato]gadolinium(III) was added to the filtrate to initiate the crystallization. The mixture was allowed to stir (low speed) overnight at room temperature. The [N,N"-Bis[N-(2-methoxyethyl)carbamoylmethyl] diethylenetriamine-N,N',N"-triacetato]gadolinium(III) crystals were collected by filtration and were washed with 375 ml of ethanol. The gadolinium complex was dried to a constant weight in vacuo. The dried product was 128.8 g (86.3% yield based on $Gd_2O_3$).

Example 10

Effect of the MEA/DTPA-bis/anhydride) Ratio on the % Yield and Purity of [N,N"-Bis[N-(2-methoxyethyl)carbamoylemethyl] diethylenetriamine-N,N',N"-triacetato]-gadolinium(III)

In this study, the 2-methoxyethylamine (MEA) ratio used in the procedure of Example 5 was varied from 1.7 to 2.2. The results from subsequent complexation with gadolinium(III) are summarized in Table III.

TABLE III

The Effect of the MEA/DTPAba Ratio on the % Yield and Purity of [N,N"-Bis[N-(2-methoxyethyl)carbamoylmethyl]diethylenetriamine-N,N',N"-triacetato]-gadolinium(III)

| MEA/ DTPAba | % Yield* | % Chrom Purity | $Gd^{3+}$ (m/m %) | Ligand (m/m %) | MEA (w/w %) |
|---|---|---|---|---|---|
| 1.7 | 72.7 | 99.8 | <0.01 | 0.01 | 0.003 |
| 1.8 | 76.1 | 99.9 | 0.03 | <0.01 | 0.003 |
| 1.9 | 80.6 | 99.6 | <0.01 | 0.03 | 0.01 |
| 2.0 | 81.2 | 98.9 | <0.01 | 0.02 | 0.003 |
| 2.1 | 82.2 | 99.8 | <0.01 | 0.01 | 0.01 |
| 2.2 | 77.8 | 99.8 | 0.03 | <0.01 | 0.01 |

*% Yield = $\frac{(Wt.\ of\ product) \times (\%\ of\ Gd\ complex\ in\ the\ product)}{Theoretical\ yield\ based\ on\ DTPA\text{-}bis(anhydride)}$ The chromatographic purity of the [N,N"-Bis[N-(2-methoxyethyl)carbamoylmethyl]diethylenetriamine-N,N',N"-triacetato]-gadolinium(III) obtained from the MEA/DTPAba= 2.0 reaction was slightly lower (98.9%). This result was probably due to carelessness in the purification steps. Based on the fact that the highest percent yields were obtained at the MEA/DTPAba ratios between 1.9 to 2.1, MEA/DTPAba=2.0 was recommended for the preparation of N,N"-Bis[N-(2-methoxyethyl)carbamoylmethyl]diethylene-triamine-N,N',N"-triacetato]-gadolinium(III).

Example 11

Effect of the Complexing Agent/$Gd_2O_3$ ratio on the % Yield and Purity of [N,N"-Bis[N-(2-methoxyethyl)carbamoylmethyl]diethylenetriamine-N,N',N"-triacetato]-gadolinium (III)

The effect of the ligand to $Gd_2O_3$ ratio on the yield and the quality of the complex was also investigated using the procedure of Example 9. The results from the final gadolinium complex obtained after crystallization are summarized in Table IV.

TABLE IV

The Effect of the Ligand/$Gd_2O_3$ Ratio on the % Yield and Purity of [N,N"-Bis[N-(2-methoxyethyl)carbamoylmethyl]diethylene-triamine-N,N',N"-triacetato]-gadolinium(III)

| Ligand/ $Gd_2O_2$ | % Yield* | Chrom Purity (%) | $Gd^{3+}$ (m/m %) | Ligand (m/m %) |
|---|---|---|---|---|
| 1.9 | 82.6 | 99.3 | 0.03 | 0.02 |
| 2.0 | 80.6 | 99.5 | <0.01 | 0.02 |
| 2.1 | 81.3 | 99.3 | <0.01 | 0.02 |
| 2.2 | 76.0 | 99.1 | <0.01 | 0.01 |
| 2.3 | 70.6 | 99.6 | <0.01 | 0.01 |

*% Yield = $\frac{(Wt.\ of\ product) \times (\%\ of\ Gd\ complex\ in\ the\ product)}{Theoretical\ yield\ based\ on\ ligand}$ The results indicated that, if the reaction was carried out using excess gadolinium oxide (ligand/$Gd_2O_3$ =1.9), the free metal in the product was higher. If the ligand/$Gd_2O_3$ 3 ratio exceeded 2.2, the percent yield of the complex was lower. The results suggest that the final gadolinium complex was best prepared using the mole ratio of ligand to $Gd_2O_3$ equal to 2.0.

Example 12

Preparation of [N,N"-Bis[N-(2-methoxyethyl)carbamoylmethyl]diethyleetriamine-N,N',N"-triacetato]-gadolinium(III) With of the DTPA-bis (amide) Complexing Agent Acetonitrile wet DTPA-bis (anhydride) containing 74.4% DTPA-bis (anhydride) (266.5 g, equivalent to 198.3 g DTPA-bis (anhydride, 0. 555 mole), 2-propanol (297.5 ml), and acetonitrile (198 ml) were mixed in a 2 L round-bottomed flask equipped with a thermometer, a mechanical stirrer, and a reflux condenser. 2-methoxyethylamine (83.4 g, 1.11 mole) was added to the reaction slurry at a rate to keep the reaction temperature at or below 65° C. The addition of MEA took about 5 minutes. The reactor was heated with stirring in a 58° C. to 60° C. oil bath for 3 hours. H20 (198 ml) was added to the solution. The solution was cooled to room temperature in an ice bath and then filtered through a filter cloth employing house vacuum.

The liltrate was transferred to a 3 L round-bottomed flask containing $Gd_2O_3$ (95.8 g, 0.264 mole). The flask was equipped with a thermometer, an overhead stirrer, and a reflux condenser. The mixture was heated at reflux (76.5° C.) with stirring in an oil bath (80°–90° C.) for 6 hours. At this time the mixture was homogeneous. The solution was cooled to room temperature and methanol (159 ml) was added to the solution. Glyme (595 ml) was slowly added to the reaction mixture. The mixture was stirred to give a homogeneous solution. A mixture (198 ml) of $H_2O$, methanol, and glyme in the ratio of 1 to 1 to 4 (v/v), respectively, was added. The entire mixture was stirred at room temperature overnight after seeding with crystalline [N,N"-Bis [N-(2-methoxyethyl)carbamoylmethyl]diethylene-triamine-N,N',N"-triacetato]-gadolinium(III). The crystalline product was collected by filtration using a filter cloth. The solid was washed with a solvent mixture (198 ml) containing H20, methanol, and glyme in the ratio of 1 to 1 to 4 (v/v), respectively. The final product was dried in a vacuum oven at 45°–50° C. to a constant weight. The dried product weighted 339.8 g (92.6% yield).

From the foregoing it will be appreciated that the use of acetonitrile in the preparation of the DTPA-bis(anhydride) simplifies handling of the DTPA-bis(anhydride) and enhances the stability of the DTPA-bis(anhydride). Acetonitrile in the preparation of the ligand and final gadolinium complex reduces the total reaction time, and the through-put of ligand and final gadolinium complex are greatly increased by increasing the concentrations of reagents in each reaction.

The elimination of the isolation of crude ligand from the reaction mixture greatly simplifies the overall manufacturing process. The percent yield of the products is increased.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process for the production of a DTPA-bis(amide) paramagnetic metal complex comprising the steps of:
   (a) reacting DTPA with acetic anhydride in pyridine and acetonitrile to produce DTPA-bis(anhydride);
   (b) isolating and washing the DTPA-bis(anhydride) with a solvent comprising acetonitrile;
   (c) suspending the DTPA-bis(anhydride) in a solvent mixture comprising 2-propanol and acetonitrile;
   (d) reacting the suspended DTPA-bis(anhydride) with a primary or secondary amine, selected from the group of $C_{1-6}$ alkylamine, $C_{1-6}$ monohydroxyalkylamine, $C_{1-6}$ polyhydroxyalkylamine, $C_{1-6}$ alkoxyalkylamine, and $C_{1-6}$ polyalkoxyalkylamine to produce a DTPA-bis(amide) complexing agent;
   (e) adding a cosolvent to solubilize the DTPA-bis(amide) complexing agent;
   (f) filtering the DTPA-bis(amide) to remove solid impurities and affecting crystallization of the DTPA-bis(amide) by addition of a crystallization solvent;
   (g) reacting the DTPA-bis(amide) with a paramagnetic metal ion, selected from a group of elements having atomic numbers of 21–25, 27–29, 42–44, and 58–70, to form a paramagnetic metal complex with the DTPA-bis(amide);
   (h) removing insoluble solids by filtration; and
   (i) crystallizing the DTPA-bis(amide) paramagnetic metal complex from the reaction mixture for final purification.

2. A process as defined in claim 1, wherein in step (b) the DTPA-bis(anhydride) is isolated as a wet solid.

3. A process as defined in claim 1, wherein in step (b) the DTPA-bis(anhydride) is isolated as a dry solid.

4. A process as defined in claim 1, wherein in step (e) the cosolvent added to solubilize the DTPA-bis(amide) is selected from the group comprising methanol, ethanol, 2-propanol, water, and mixtures thereof.

5. A process as defined in claim 1, wherein in step (f) the crystallization solvent is selected from the group comprising glyme, ethanol, 2-propanol, acetonitrile, methanol, and mixtures thereof.

6. A process as defined in claim 1, wherein in step (i) the paramagnetic metal complex with the DTPA-bis(amide) is crystallized from the product mixture by the addition of ethanol and acetonitrile to the mixture.

7. A process as defined in claim 1, wherein in step (i) the paramagnetic metal complex with the DTPA-bis(amide) is crystallized from the product mixture by the addition of methanol and glyme to the mixture.

8. A process as defined in claim 1, wherein in step (i) the paramagnetic metal complex with the DTPA-bis(amide) is crystallized from the product mixture by the addition of acetonitrile to the mixture.

9. A process for the production of [N,N"-Bis[N-(2-methoxyethyl)carbamoylmethyl]diethylenetriamine-N,N',N"-triacetato]-gadolinium(III) comprising the steps of:
   (a) reacting DTPA with acetic anhydride in pyridine and acetonitrile to produce DTPA-bis(anhydride);
   (b) isolating and washing the DTPA-bis(anhydride) with a solvent comprising acetonitrile;
   (c) suspending the DTPA-bis(anhydride) in a solvent mixture comprising 2-propanol and acetonitrile;
   (d) reacting the suspended DTPA-bis(anhydride) with 2-methoxyethylamine to produce N,N"-Bis[N-(2-methoxyethyl)carbamoylmethyl]diethylenetriamine-N, N',N"-triacetic acid;
   (e) adding a cosolvent to solubilize the N,N"-Bis[N-(2-methoxyethyl)carbamoylmethyl]diethylenetriamine-N, N',N"-triacetic acid;
   (f) filtering the N,N"-Bis[N-(2-methoxyethyl)carbamoylmethyl]diethylenetriamine-N,N',N"-triacetic acid to remove solid impurities and affecting crystallizatoin of the N,N"-Bis[N-(2-methoxyethyl)carbamoylmethyl] diethylenetriamine-N,N",N"-triacetic acid by addition of a crystallization solvent;
   (g) reacting N,N"-Bis[N-(2-methoxyethyl)carbamoylmethyl]diethylenetriamine-N,N',N"-triacetic acid with gadolinium oxide to form [N,N"-Bis[N-(2-methoxyethyl)carbamoylmethyl]diethylenetriamine-N,N',N"-triacetato]-gadolinium(III);
   (h) removing insoluble solids by filtration; and
   (i) crystallizing [N,N"-Bis[N-(2-methoxyethyl)carbamoylmethyl]diethylenetriamine-N,N',N"-triacetato]-gadolinium(III) from the reaction mixture for final purification.

10. A process as defined in claim 9, wherein in step (b) the solvent used to isolate and wash the DTPA-bis(anhydride) further comprises 2-propanol.

11. A process as defined in claim 9, wherein in step (b) the DTPA-bis(anhydride) is isolated as a wet solid.

12. A process as defined in claim 9, wherein in step (b) the DTPA-bis(anhydride) is isolated as a dry solid.

13. A process as defined in claim 9, wherein in step (c) the cosolvent added to solubilize the N,N"-Bis[N-(2-methoxyethyl)carbamoylmethyl]diethylenetriamine-N,N',N"-triacetic acid comprises methanol.

14. A process as defined in claim 9, wherein in step (e) the cosolvent added to solubilize the N,N"-Bis[N-(2-methoxyethyl)carbamoylmethyl]diethylenetriamine-N,N',N''-triacetic acid comprises ethanol.

15. A process as defined in claim 9, wherein in step (e) the cosolvent added to solubilize the N,N''-Bis[N-(2-methoxyethyl)carbamoylmethyl]diethylenetriamine-N,N',N''-triacetic acid comprises ethanol and 2-propanol.

16. A process as defined in claim 9, wherein in step (e) the cosolvent added to solubilize the N,N''-Bis[N-(2-methoxyethyl)carbamoylmethyl]diethylenetriamine-N,N',N''-triacetic acid comprises water.

17. A process as defined in claim 10, wherein in step (f) the crystallization solvent comprises glyme.

18. A process as defined in claim 10, wherein in step (f) the crystallization solvent comprises ethanol.

19. A process as defined in claim 10, wherein in step (f) the crystallization solvent comprises 2-propanol.

20. A process as defined in claim 10, wherein in step (f) the crystallization solvent comprises acetonitrile.

21. A process as defined in claim 9, wherein in step (i) [N,N''-Bis[N-(2-methoxyethyl)carbamoylmethyl]-diethylenetriamine, N,N'-,N''-triacetato]-gadolinium(III) is crystallized from the product mixture by the addition of ethanol and acetonitrile to the mixture.

22. A process as defined in claim 9, wherein in step (i) [N,N''-Bis [N-(2-methoxyethyl)carbamoylmethyl]diethylenetriamine, N,N'-,N''-triacetato]-gadolinium(III) is crystallized from the product mixture by the addition of methanol and glyme to the mixture.

23. A process as defined in claim 9, wherein in step (i) [N,N''-Bis [N-(2-methoxyethyl)carbamoylmethyl]diethylenetriamine, N,N'-,N''-triacetato]-gadolinium(III) is crystallized from the product mixture by the addition of acetonitrile to the mixture.

* * * * *